(12) United States Patent
Welinder et al.

(10) Patent No.: US 6,258,769 B1
(45) Date of Patent: Jul. 10, 2001

(54) PEROXIDASE VARIANTS WITH IMPROVED HYDROGEN PEROXIDE STABILITY

(75) Inventors: Karen Gjesing Welinder, Virum; Morten Birket Andersen, Copenhagen, both of (DK)

(73) Assignee: Novozymes A/S Patents, Bagsvaed (DK)

( * ) Notice: Subject to any disclaimer, the term of this patent is extended or adjusted under 35 U.S.C. 154(b) by 0 days.

(21) Appl. No.: 09/168,406

(22) Filed: Oct. 6, 1998

Related U.S. Application Data

(62) Division of application No. 08/331,515, filed on Nov. 1, 1994, now Pat. No. 5,851,811, which is a continuation of application No. PCT/DK93/00189, filed on Jun. 1, 1993.

(30) Foreign Application Priority Data

Jun. 1, 1992 (DK) .................................................. 0729/92

(51) Int. Cl.[7] .......................... C11D 3/386; C11D 3/395; C12N 9/08; C12N 15/53; C12N 15/09
(52) U.S. Cl. ..................... 510/374; 435/192; 435/440; 435/471; 510/392; 536/23.2
(58) Field of Search .................................... 435/192, 440, 435/471; 536/23.2; 510/374, 392

(56) References Cited

U.S. PATENT DOCUMENTS

| 4,732,973 | * | 3/1988 | Barr et al. ........................ 530/350 |
| 4,752,585 | * | 6/1988 | Koths et al. ...................... 435/256 |
| 5,286,638 | * | 2/1994 | Tanaka et al. .................... 435/192 |
| 5,346,823 | * | 9/1994 | Estell et al. ...................... 435/222 |

FOREIGN PATENT DOCUMENTS

| 179486 | 4/1986 | (EP) . |
| 505311 | 9/1991 | (EP) . |
| 486067 | 5/1992 | (EP) . |
| WO 91/05858 | 2/1991 | (WO) . |
| 91/05839 | * 5/1991 | (WO) . |

OTHER PUBLICATIONS

M. Kjalke et al. "Comparison of Structure and Activities of Peroxidases from *Coprinus cinereus, Coprinus macrorhizus,* and *Arthromyces ramosus*", Biochem. Biophys. Acta 1120: 248–256, Apr. 1992.*

K. Welinder et al. "Structure of Plant and Fungal Peroxidases", Biochem. Soc. Trans. 20: 337–340, May 1992.*

* cited by examiner

*Primary Examiner*—Rebecca E. Prouty
(74) *Attorney, Agent, or Firm*—Elias Lambiris, Esq.

(57) ABSTRACT

A variant of a *Coprinus cinereus* peroxidase having one or more substitutions selected from M166L, V, I, F, Q and M242L, V, I, F, Q, wherein the parent peroxidase is encoded by the DNA sequence shown of SEQ ID:1.

14 Claims, 1 Drawing Sheet

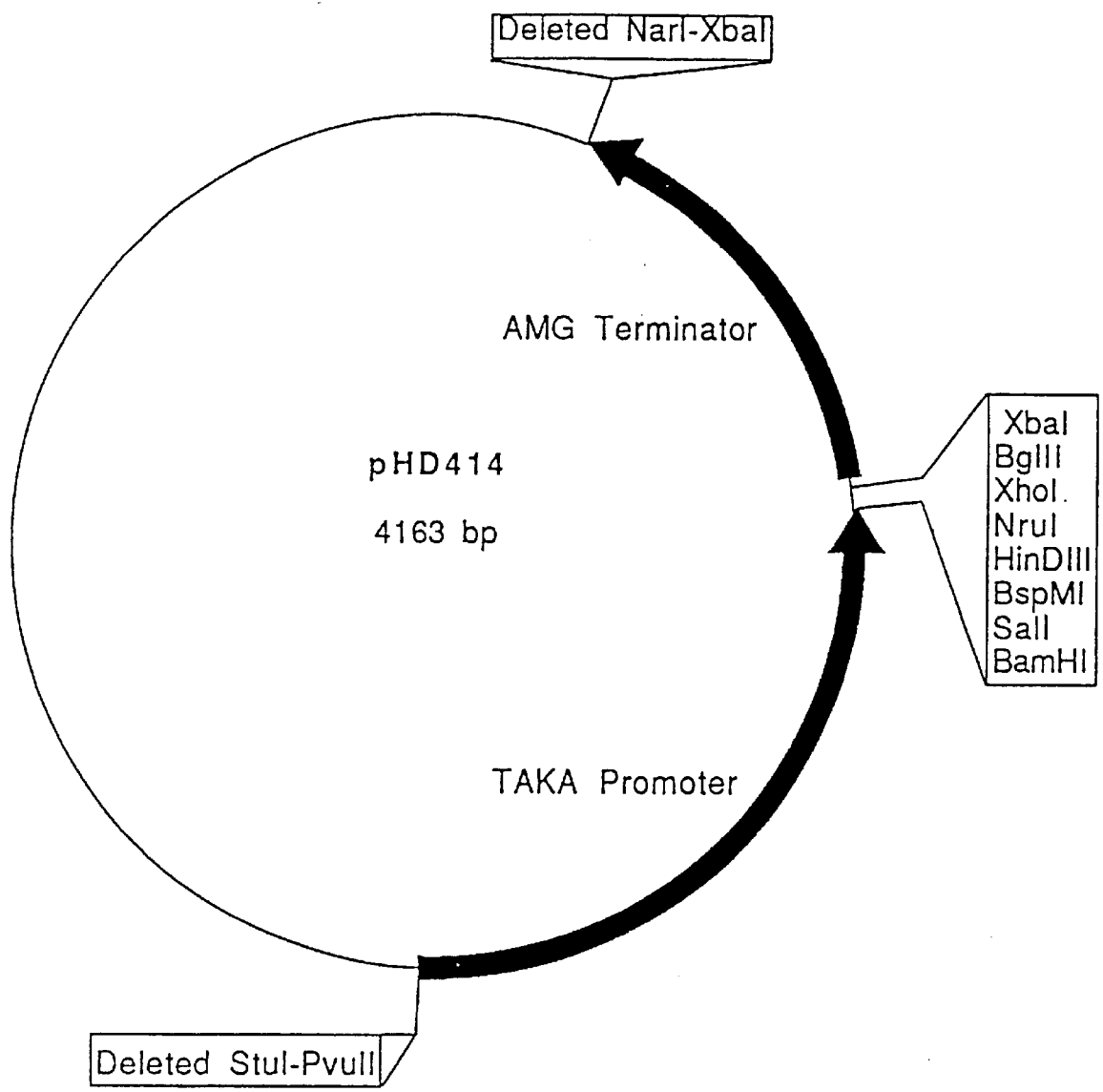

SEQUENCE LISTING

<160> NUMBER OF SEQ ID NOS: 43

<210> SEQ ID NO 1
<211> LENGTH: 1306
<212> TYPE: DNA
<213> ORGANISM: Coprinus cinereus

<400> SEQUENCE: 1

```
actatgaagc tctcgctttt gtccaccttc gctgctgtca tcatcggtgc cctcgctcta      60
ccccagggtc ctggaggagg cgggtcagtc acttgccccg gtggacagtc cacttcgaac     120
agccagtgct gcgtctggtt cgacgttcta gacgatcttc agaccaactt ctaccaaggg     180
tccaagtgtg agagccctgt tcgcaagatt cttagaattg ttttccatga cgcgatcgga     240
ttttcgccgg cgttgactgc tgctggtcaa ttcgtggtg gaggagctga tggctccatc      300
attgcgcatt cgaacatcga attggccttc ccggctaatg gcggcctcac cgacaccgtc     360
gaagccctcc gcgcggtcgg tatcaaccac ggtgtctctt cggcgatct catccaattc      420
```

```
gccactgccg tcggcatgtc caactgccct ggctctcccc gacttgagtt cttgacgggc    480
aggagcaaca gttcccaacc ctcccctcct tcgttgatcc ccggtccgg  aaacactgtc    540 actgctatct tggatcgtat gggcgatgca ggcttcagcc ctgatgaagt agttgacttg    600
cttgctgcgc atagtttggc ttctcaggag ggtttgaact cggccatctt caggtctcct    660
ttggactcga cccctcaagt tttcgatacc cagttctaca ttgagacctt gctcaaggg t   720 accactcagc ctggcccttc tctcggcttt gcagaggagc tctccccctt ccctggcgaa    780
ttccgcatga ggtccgatgc tctcttggct cgcgactccc gaaccgcctg ccgatggcaa    840
tccatgacca gcagcaatga agttatgggc cagcgatacc gcgccgccat ggccaagatg    900
tctgttctcg gcttcgacag gaacgccctc accgattgct ctgacgttat tccttctgct    960
gtgtccaaca acgctgctcc tgttatccct ggtggcctta ctgtcgatga tatcgaggtt   1020
tcgtgcccga gcgagccttt ccctgaaatt gctaccgcct caggccctct ccctcccctc   1080
gctcctgctc cttgatctgg tgaagatggt acatcctgct ctctcatcat ccctcttagc   1140
tatttatcca atctatctac ctatctatgc agtttctgtt ctatcaccac aggaagcaag   1200
aaagaaaaac aacaatgcaa cgtgagcaga aatcagcaaa aaaataaatc agtatactac   1260
agtaatgagg ccagtttgcg tggtgtcaga agtaagtacg actcgg                   1306
```

<210> SEQ ID NO 2
<211> LENGTH: 435
<212> TYPE: PRT
<213> ORGANISM: Coprinus cinereus
<220> FEATURE:
<221> NAME/KEY: VARIANT
<222> LOCATION: (1)...(435)
<223> OTHER INFORMATION: Xaa = Any Amino Acid

<400> SEQUENCE: 2

```
Thr Met Lys Leu Ser Leu Leu Ser Thr Phe Ala Ala Val Ile Ile Gly
 1               5                  10                  15

Ala Leu Ala Leu Pro Gln Gly Pro Gly Gly Gly Ser Val Thr Cys
            20                  25                  30

Pro Gly Gly Gln Ser Thr Ser Asn Ser Gln Cys Cys Val Trp Phe Asp
         35                  40                  45

Val Leu Asp Asp Leu Gln Thr Asn Phe Tyr Gln Gly Ser Lys Cys Glu
     50                  55                  60

Ser Pro Val Arg Lys Ile Leu Arg Ile Val Phe His Asp Ala Ile Gly
 65                  70                  75                  80

Phe Ser Pro Ala Leu Thr Ala Ala Gly Gln Phe Gly Gly Gly Ala
                 85                  90                  95

Asp Gly Ser Ile Ile Ala His Ser Asn Ile Glu Leu Ala Phe Pro Ala
            100                 105                 110

Asn Gly Gly Leu Thr Asp Thr Val Glu Ala Leu Arg Ala Val Gly Ile
        115                 120                 125

Asn His Gly Val Ser Phe Gly Asp Leu Ile Gln Phe Ala Thr Ala Val
    130                 135                 140

Gly Met Ser Asn Cys Pro Gly Ser Pro Arg Leu Glu Phe Leu Thr Gly
145                 150                 155                 160

Arg Ser Asn Ser Ser Gln Pro Ser Pro Ser Leu Ile Pro Gly Pro
                165                 170                 175

Gly Asn Thr Val Thr Ala Ile Leu Asp Arg Met Gly Asp Ala Gly Phe
            180                 185                 190
```

```
Ser Pro Asp Glu Val Val Asp Leu Leu Ala Ala His Ser Leu Ala Ser
        195                 200                 205

Gln Glu Gly Leu Asn Ser Ala Ile Phe Arg Ser Pro Leu Asp Ser Thr
    210                 215                 220

Pro Gln Val Phe Asp Thr Gln Phe Tyr Ile Glu Thr Leu Leu Lys Gly
225                 230                 235                 240

Thr Thr Gln Pro Gly Pro Ser Leu Gly Phe Ala Glu Glu Leu Ser Pro
                245                 250                 255

Phe Pro Gly Glu Phe Arg Met Arg Ser Asp Ala Leu Leu Ala Arg Asp
            260                 265                 270

Ser Arg Thr Ala Cys Arg Trp Gln Ser Met Thr Ser Ser Asn Glu Val
        275                 280                 285

Met Gly Gln Arg Tyr Arg Ala Ala Met Ala Lys Met Ser Val Leu Gly
    290                 295                 300

Phe Asp Arg Asn Ala Leu Thr Asp Cys Ser Asp Val Ile Pro Ser Ala
305                 310                 315                 320

Val Ser Asn Asn Ala Ala Pro Val Ile Pro Gly Gly Leu Thr Val Asp
                325                 330                 335

Asp Ile Glu Val Ser Cys Pro Ser Glu Pro Phe Pro Glu Ile Ala Thr
            340                 345                 350

Ala Ser Gly Pro Leu Pro Ser Leu Ala Pro Ala Pro Xaa Ser Gly Glu
        355                 360                 365

Asp Gly Thr Ser Cys Ser Leu Ile Ile Pro Leu Ser Tyr Leu Ser Asn
    370                 375                 380

Leu Ser Thr Tyr Leu Cys Ser Phe Cys Ser Ile Thr Thr Gly Ser Lys
385                 390                 395                 400

Lys Glu Lys Gln Gln Cys Asn Val Ser Arg Asn Gln Lys Asn Lys
                405                 410                 415

Ser Val Tyr Tyr Ser Asn Glu Ala Ser Leu Arg Gly Val Arg Ser Lys
        420                 425                 430

Tyr Asp Ser
        435

<210> SEQ ID NO 3
<211> LENGTH: 27
<212> TYPE: DNA
<213> ORGANISM: Artificial Sequence
<220> FEATURE:
<223> OTHER INFORMATION: Primer
<221> NAME/KEY: misc_feature
<222> LOCATION: (1)...(27)
<223> OTHER INFORMATION: n = A,T,C or G

<400> SEQUENCE: 3
gcgcgaattc gtnggnatna accacgg                                   27

<210> SEQ ID NO 4
<211> LENGTH: 25
<212> TYPE: DNA
<213> ORGANISM: Artificial Sequence
<220> FEATURE:
<223> OTHER INFORMATION: Primer
<221> NAME/KEY: misc_feature
<222> LOCATION: (1)...(25)
<223> OTHER INFORMATION: n = A,T,C or G

<400> SEQUENCE: 4
gcggatccgg ngggcagtwn gacat                                     25
```

```
<210> SEQ ID NO 5
<211> LENGTH: 28
<212> TYPE: DNA
<213> ORGANISM: Artificial Sequence
<220> FEATURE:
<223> OTHER INFORMATION: Primer
<221> NAME/KEY: misc_feature
<222> LOCATION: (1)...(28)
<223> OTHER INFORMATION: n = A,T,C or G

<400> SEQUENCE: 5
gcgaattcac nmcncaggtn ttcgacac                                28

<210> SEQ ID NO 6
<211> LENGTH: 26
<212> TYPE: DNA
<213> ORGANISM: Artificial Sequence
<220> FEATURE:
<223> OTHER INFORMATION: Primer
<221> NAME/KEY: misc_feature
<222> LOCATION: (1)...(26)
<223> OTHER INFORMATION: n = A,T,C or G

<400> SEQUENCE: 6
gcggatccga actcnccngg gaangg                                  26

<210> SEQ ID NO 7
<211> LENGTH: 21
<212> TYPE: DNA
<213> ORGANISM: Artificial Sequence
<220> FEATURE:
<223> OTHER INFORMATION: Primer
<221> NAME/KEY: misc_feature
<222> LOCATION: (1)...(21)
<223> OTHER INFORMATION: n = A,T,C or G

<400> SEQUENCE: 7
gcgcgaattc wggcagtcna c                                       21

<210> SEQ ID NO 8
<211> LENGTH: 22
<212> TYPE: DNA
<213> ORGANISM: Artificial Sequence
<220> FEATURE:
<223> OTHER INFORMATION: Primer
<221> NAME/KEY: misc_feature
<222> LOCATION: (1)...(22)
<223> OTHER INFORMATION: n = A,T,C or G

<400> SEQUENCE: 8
gcgcgaattc tggcagarna tg                                      22

<210> SEQ ID NO 9
<211> LENGTH: 23
<212> TYPE: DNA
<213> ORGANISM: Artificial Sequence
<220> FEATURE:
<223> OTHER INFORMATION: Primer
<221> NAME/KEY: misc_feature
<222> LOCATION: (1)...(23)
<223> OTHER INFORMATION: n = A,T,C or G

<400> SEQUENCE: 9
ggatccgaca tcttngccat ngc                                     23

<210> SEQ ID NO 10
<211> LENGTH: 17
<212> TYPE: DNA
<213> ORGANISM: Artificial Sequence
```

```
<220> FEATURE:
<223> OTHER INFORMATION: Primer

<400> SEQUENCE: 10
gtytyratrt araaytg                                                17

<210> SEQ ID NO 11
<211> LENGTH: 15
<212> TYPE: DNA
<213> ORGANISM: Artificial Sequence
<220> FEATURE:
<223> OTHER INFORMATION: Primer

<400> SEQUENCE: 11
caggagttcc caacc                                                  15

<210> SEQ ID NO 12
<211> LENGTH: 33
<212> TYPE: DNA
<213> ORGANISM: Artificial Sequence
<220> FEATURE:
<223> OTHER INFORMATION: Primer

<400> SEQUENCE: 12
tgatcatagt accatctaat tacatcaagc ggc                              33

<210> SEQ ID NO 13
<211> LENGTH: 18
<212> TYPE: DNA
<213> ORGANISM: Artificial Sequence
<220> FEATURE:
<223> OTHER INFORMATION: Primer

<400> SEQUENCE: 13
ctgtaatacg actcacta                                               18

<210> SEQ ID NO 14
<211> LENGTH: 18
<212> TYPE: DNA
<213> ORGANISM: Artificial Sequence
<220> FEATURE:
<223> OTHER INFORMATION: Primer

<400> SEQUENCE: 14
tgatcagact agtaccat                                               18

<210> SEQ ID NO 15
<211> LENGTH: 22
<212> TYPE: DNA
<213> ORGANISM: Artificial Sequence
<220> FEATURE:
<223> OTHER INFORMATION: Primer

<400> SEQUENCE: 15
caggagcact agttcccaac cc                                          22

<210> SEQ ID NO 16
<211> LENGTH: 18
<212> TYPE: DNA
<213> ORGANISM: Artificial Sequence
<220> FEATURE:
<223> OTHER INFORMATION: Primer

<400> SEQUENCE: 16
ttttccataa cgcgatcg                                               18
```

```
<210> SEQ ID NO 17
<211> LENGTH: 18
<212> TYPE: DNA
<213> ORGANISM: Artificial Sequence
<220> FEATURE:
<223> OTHER INFORMATION: Primer

<400> SEQUENCE: 17
ggtcccttta acactgtc                                                18

<210> SEQ ID NO 18
<211> LENGTH: 20
<212> TYPE: DNA
<213> ORGANISM: Artificial Sequence
<220> FEATURE:
<223> OTHER INFORMATION: Primer

<400> SEQUENCE: 18
caggagcccg agttcccaac                                              20

<210> SEQ ID NO 19
<211> LENGTH: 20
<212> TYPE: DNA
<213> ORGANISM: Artificial Sequence
<220> FEATURE:
<223> OTHER INFORMATION: Primer

<400> SEQUENCE: 19
caggagcgac tcttcccaac                                              20

<210> SEQ ID NO 20
<211> LENGTH: 28
<212> TYPE: DNA
<213> ORGANISM: Artificial Sequence
<220> FEATURE:
<223> OTHER INFORMATION: Primer

<400> SEQUENCE: 20
gatccccgag cccttcgaaa ctgtcact                                     28

<210> SEQ ID NO 21
<211> LENGTH: 25
<212> TYPE: DNA
<213> ORGANISM: Artificial Sequence
<220> FEATURE:
<223> OTHER INFORMATION: Primer

<400> SEQUENCE: 21
gatccccgag ccctttaaca ctgtc                                        25

<210> SEQ ID NO 22
<211> LENGTH: 23
<212> TYPE: DNA
<213> ORGANISM: Artificial Sequence
<220> FEATURE:
<223> OTHER INFORMATION: Primer

<400> SEQUENCE: 22
ggtcccttct tcactgtcac tgc                                          23

<210> SEQ ID NO 23
<211> LENGTH: 21
<212> TYPE: DNA
<213> ORGANISM: Artificial Sequence
<220> FEATURE:
<223> OTHER INFORMATION: Primer
```

<400> SEQUENCE: 23
tcccggattt actgtcactg c                                             21

<210> SEQ ID NO 24
<211> LENGTH: 20
<212> TYPE: DNA
<213> ORGANISM: Artificial Sequence
<220> FEATURE:
<223> OTHER INFORMATION: Primer

<400> SEQUENCE: 24
gttttccata ctgcgatcgg                                               20

<210> SEQ ID NO 25
<211> LENGTH: 20
<212> TYPE: DNA
<213> ORGANISM: Artificial Sequence
<220> FEATURE:
<223> OTHER INFORMATION: Primer

<400> SEQUENCE: 25
gttttccata ttgcgatcgg                                               20

<210> SEQ ID NO 26
<211> LENGTH: 20
<212> TYPE: DNA
<213> ORGANISM: Artificial Sequence
<220> FEATURE:
<223> OTHER INFORMATION: Primer

<400> SEQUENCE: 26
atgaggtcga tcgctctctt                                               20

<210> SEQ ID NO 27
<211> LENGTH: 20
<212> TYPE: DNA
<213> ORGANISM: Artificial Sequence
<220> FEATURE:
<223> OTHER INFORMATION: Primer

<400> SEQUENCE: 27
atgaggtcca cggctctctt                                               20

<210> SEQ ID NO 28
<211> LENGTH: 20
<212> TYPE: DNA
<213> ORGANISM: Artificial Sequence
<220> FEATURE:
<223> OTHER INFORMATION: Primer

<400> SEQUENCE: 28
atgaggtcca atgctctctt                                               20

<210> SEQ ID NO 29
<211> LENGTH: 19
<212> TYPE: DNA
<213> ORGANISM: Artificial Sequence
<220> FEATURE:
<223> OTHER INFORMATION: Primer

<400> SEQUENCE: 29
aacagccaga gctgcgtct                                                19

<210> SEQ ID NO 30

```
<211> LENGTH: 20
<212> TYPE: DNA
<213> ORGANISM: Artificial Sequence
<220> FEATURE:
<223> OTHER INFORMATION: Primer

<400> SEQUENCE: 30
agccagtgca gcgtctggtt                                              20

<210> SEQ ID NO 31
<211> LENGTH: 21
<212> TYPE: DNA
<213> ORGANISM: Artificial Sequence
<220> FEATURE:
<223> OTHER INFORMATION: Primer

<400> SEQUENCE: 31
gctctaccct ccggacctgg a                                            21

<210> SEQ ID NO 32
<211> LENGTH: 21
<212> TYPE: DNA
<213> ORGANISM: Artificial Sequence
<220> FEATURE:
<223> OTHER INFORMATION: Primer

<400> SEQUENCE: 32
gctctacccg agggtcctgg a                                            21

<210> SEQ ID NO 33
<211> LENGTH: 18
<212> TYPE: DNA
<213> ORGANISM: Artificial Sequence
<220> FEATURE:
<223> OTHER INFORMATION: Primer

<400> SEQUENCE: 33
aacaactgag ctcctgtt                                                18

<210> SEQ ID NO 34
<211> LENGTH: 18
<212> TYPE: DNA
<213> ORGANISM: Artificial Sequence
<220> FEATURE:
<223> OTHER INFORMATION: Primer

<400> SEQUENCE: 34
accgcctcgc gatggcaa                                                18

<210> SEQ ID NO 35
<211> LENGTH: 21
<212> TYPE: DNA
<213> ORGANISM: Artificial Sequence
<220> FEATURE:
<223> OTHER INFORMATION: Primer

<400> SEQUENCE: 35
ttgatccccg agcccggaaa c                                            21

<210> SEQ ID NO 36
<211> LENGTH: 21
<212> TYPE: DNA
<213> ORGANISM: Artificial Sequence
<220> FEATURE:
<223> OTHER INFORMATION: Primer

<400> SEQUENCE: 36
```

```
ggtcccggag aaactgtcac t                                         21

<210> SEQ ID NO 37
<211> LENGTH: 39
<212> TYPE: DNA
<213> ORGANISM: Artificial Sequence
<220> FEATURE:
<223> OTHER INFORMATION: Primer

<400> SEQUENCE: 37
attgctgcag cctcaggccc tctcccagcg ctcgctcct                      39

<210> SEQ ID NO 38
<211> LENGTH: 39
<212> TYPE: DNA
<213> ORGANISM: Artificial Sequence
<220> FEATURE:
<223> OTHER INFORMATION: Primer

<400> SEQUENCE: 38
attgctaatg cctcaggccc tctcccagcg ctcgctcct                      39

<210> SEQ ID NO 39
<211> LENGTH: 21
<212> TYPE: DNA
<213> ORGANISM: Artificial Sequence
<220> FEATURE:
<223> OTHER INFORMATION: Primer

<400> SEQUENCE: 39
ggggcacgtg acgttcccgc c                                         21

<210> SEQ ID NO 40
<211> LENGTH: 24
<212> TYPE: DNA
<213> ORGANISM: Artificial Sequence
<220> FEATURE:
<223> OTHER INFORMATION: Primer

<400> SEQUENCE: 40
cataacttcg ctgctattgg tcat                                      24

<210> SEQ ID NO 41
<211> LENGTH: 21
<212> TYPE: DNA
<213> ORGANISM: Artificial Sequence
<220> FEATURE:
<223> OTHER INFORMATION: Primer

<400> SEQUENCE: 41
cttggaccca ttgtagaagt t                                         21

<210> SEQ ID NO 42
<211> LENGTH: 21
<212> TYPE: DNA
<213> ORGANISM: Artificial Sequence
<220> FEATURE:
<223> OTHER INFORMATION: Primer

<400> SEQUENCE: 42
aacaggagcg ctgttgttgg a                                         21

<210> SEQ ID NO 43
<211> LENGTH: 21
<212> TYPE: DNA
```

```
<213> ORGANISM: Artificial Sequence
<220> FEATURE:
<223> OTHER INFORMATION: Primer

<400> SEQUENCE: 43
ctcgctctaa tggagggtcc t                                                    21
```

PEROXIDASE VARIANTS WITH IMPROVED HYDROGEN PEROXIDE STABILITY

CROSS-REFERENCE TO RELATED APPLICATIONS

This application is a divisional of application Ser. No. 08/331,515 filed on Nov. 1, 1994 now U.S. Pat. No. 5,851, 811, which is a continuation of application Ser. No. PCT/DK93/00189 filed on Jun. 1, 1993, and claims priority under 35 U.S.C. 119 of Danish application serial no. 0729/92 filed Jun. 1, 1992, the contents of which are fully incorporated herein by reference.

FIELD OF INVENTION

The present invention relates to a novel variant of peroxidase, and a bleaching agent or detergent composition comprising the peroxidase variant.

BACKGROUND OF THE INVENTION

The use of bleaching agents in washing procedures and as constituents of detergent compositions is well known in the art. Thus, bleaching agents are incorporated in or sold as constituents of a major part of the commercially available detergent compositions. Important conventional bleaching agents incorporated in detergent compositions are compounds which act as precursors of hydrogen peroxide formed in the course of the washing procedure. Perborates and percarbonates are the most important examples of compounds which are employed as bleaching agents and which exert a bleaching effect in this fashion. The detailed mechanism of bleaching by means of these bleaching agents is not known at present, but it is generally assumed that the hydrogen peroxide formed during washing converts coloured substances (responsible for stains on fabric) into non-coloured materials by oxidation and that some oxidation of the coloured substances may also take place due to their direct interaction with perborate or percarbonate.

One drawback of these commonly used bleaching agents is that they are not particularly efficient at the lower temperatures at which coloured fabrics are usually washed. Their efficiency may be enhanced by the use of activators (e.g. organic acid anhydrides, esters or imides) which give rise to the formation of peracids.

Apart from being employed for bleaching stains on fabric, such conventional bleaching agents have also been suggested for preventing surplus dyes from coloured fabrics which leach from the fabrics when these are washed from being deposited on other fabrics present in the same wash (this phenomenon is commonly known as dye transfer). The problem of dye transfer, of course, is most noticeable when white or light-coloured fabrics are washed together with fabrics of a darker colour from which dye is leached during washing.

It has been found that peroxidases utilizing hydrogen peroxide as their substrate are able to enhance the bleaching effect of hydrogen peroxide during washing. The use of peroxidase for bleaching stains on fabrics is described in WO 89/09813. It was also found that coloured substances leached from dyed fabrics could be bleached by means of peroxidases. The use of peroxidase for inhibiting the transfer of dye from a dyed fabric to another fabric during washing is described in WO 91/05839.

SUMMARY OF THE INVENTION

It has surprisingly been found that peroxidase variants with an improved stability towards hydrogen peroxide may be prepared by recombinant DNA techniques.

Accordingly, the present invention relates to a peroxidase variant with improved hydrogen peroxide stability, characterized by insertion, deletion or substitution of one or more amino acid residues located in or near the substrate channel of the parent peroxidase, near the heme group of the parent peroxidase or at or near the active site of the parent peroxidase.

Information about the three-dimensional structure of the parent peroxidase was obtained by aligning the amino acid sequence of the parent peroxidase to amino acid sequences of other known peroxidases (K. G. Welinder et al., "Structure and evolution of peroxidases" in Plant Peroxidase Biochemistry and Physiology, K. G. Welinder et al. (eds.), University of Copenhagen and Geneva 1993, in press). The sequence alignment showed that the parent peroxidase was homologous to yeast cytochrome c peroxidase (CCP) which has a known structure (J. Wang et al. , Biochemistry 29, 1990, p. 7160), and the overall structure of the parent peroxidase could therefore be inferred from the CCP structure. An example of how structural information for a homologous peroxidase can be inferred from the crystal structure of CCP is given in P. Du et al., Protein Engineering 5, 1992, pp. 679–691.

In the present context, the term "substrate channel" is intended to indicate a passage in the peroxidase molecule through which the substrate passes before oxidation at the heme group of the peroxidase. The term "active site" is intended to indicate the substrate-binding site of the peroxidase (cf. Eur. J. Biochem. 213, 1993, pp 605–611). The term "near" should be taken to indicate a distance from the substrate channel, heme group or active site, respectively, of not more than 15 Å, more preferably not more than 10 Å, most preferably not more than 5Å, in any direction. The term "stability" is intended to indicate that the enzyme is active in the presence of hydrogen peroxide at a concentration of up to 20 mM.

In another aspect, the present invention relates to a bleaching agent comprising a peroxidase variant according to the invention, optionally in the form of a non-dusting granulate, a liquid, in particular a stabilised liquid, or a protected enzyme.

BRIEF DESCRIPTION OF THE DRAWING

FIG. 1 is a schematic representation of the plasmid pHD414.

DETAILED DISCLOSURE OF THE INVENTION

In the present description and claims, the following abbreviations are used:

| A | = | Ala | = | Alanine |
|---|---|-----|---|---------|
| V | = | Val | = | Valine |
| L | = | Leu | = | Leucine |
| I | = | Ile | = | Isoleucine |
| P | = | Pro | = | Proline |
| F | = | Phe | = | Phenylalanine |
| W | = | Trp | = | Tryptophan |
| M | = | Met | = | Methionine |
| G | = | Gly | = | Glycine |
| S | = | Ser | = | Serine |
| T | = | Thr | = | Threonine |
| C | = | Cys | = | Cysteine |
| Y | = | Tyr | = | Tyrosine |
| N | = | Asn | = | Asparagine |
| Q | = | Gln | = | Glutamine |

-continued

| D | = | Asp | = | Aspartic Acid |
| E | = | Glu | = | Glutamic Acid |
| K | = | Lys | = | Lysine |
| R | = | Arg | = | Arginine |
| H | = | His | = | Histidine |

In describing peroxidase variants according to the invention, the following nomenclature is used for ease of reference: Original amino acid(s):position(s):substituted amino acid(s)

According to this nomenclature, for instance the substitution of glutamic acid for glycine in position 154 is shown as:

G154E a deletion of glycine in the same position is shown as:

G154* and insertion of an additional amino acid residue such as lysine is shown as:

G154GK

Multiple mutations are separated by pluses, i.e.:

G154E+G156F representing mutations in positions 154 and 156 substituting glutamic acid and phenylalanine for glycine and glycine, respectively.

The parent peroxidase may suitably be a microbial, in particular a fungal, peroxidase, preferably a Coprinus sp. or Arthromyces sp. peroxidase, in particular a *Coprinus cinereus* peroxidase.

In a preferred embodiment of the peroxidase variant according to the invention, the parent peroxidase is encoded by the DNA sequence shown in SEQ ID No. 1. Said sequence is derivable from *Coprinus cinereus*.

In one embodiment of the peroxidase variant of the invention, one or more amino acid residues are deleted, inserted or substituted in the region from amino acid residue 79 to 94, 125, 153 to 157, 161 to 204, 242, 276 or 279 of the parent peroxidase encoded by the DNA sequence shown in SEQ ID No. 1.

In other embodiments of the peroxidase variant according to the invention, one or more amino acid residues may suitably be substituted as follows Q1S,E,
S8N,
C22S,
C23S,
Q38N,
D56N,T,I,
M125L,V,I,F,Q,
N142S,T,P,D,
G154E,
G156F,
N157E,F,
M166L,V,I,F,Q,
M242L,V,I,F,Q,
D245I,T,N,
C256S,
S263N,
N265S,
M276I,F,L,V,Q,
M279L,V,I,F,Q,
A304S,
T331A,N,
S338A In an alternative embodiment, the peroxidase variant according to the invention may be a fragment of the parent peroxidase, e.g. a fragment from amino acid residue 1 to amino acid residue 304 of the peroxidase sequence encoded by the DNA sequence shown in SEQ ID No. 1.

According to the invention, two or more amino acid residues of the peroxidase sequence may also be substituted as follows G154E+G156F+N157E
G154E+G156F
G156F+N157F
T331A+S338A
S263N+N265S
T331N+S338A
T331N+S338A+N142
T331N+S338A+S263N+N265S+S8N
T331N+S338A+S263N+N265S+S8N+Q38N+A304S The DNA sequence encoding a parent peroxidase may be isolated from any microorganism producing the peroxidase in question by various methods well known in the art. First a genomic DNA and/or cDNA library should be constructed using chromosomal DNA or messenger RNA from the organism that produces the peroxidase to be studied. Then, if the amino acid sequence of the peroxidase is known, homologous, labelled oligonucleotide probes may be synthesized and used to identify peroxidase-encoding clones from a genomic library of bacterial DNA, or from a fungal cDNA library. Alternatively, a labelled oligonucleotide probe containing sequences homologous to peroxidase from another strain of fungus could be used as a probe to identify peroxidase-encoding clones, using hybridization and washing conditions of lower stringency.

Another method for identifying peroxidase-producing clones involves inserting fragments of genomic DNA into an expression vector, such as a plasmid, transforming peroxidase-negative bacteria with the resulting genomic DNA library, and then plating the transformed bacteria onto agar containing a substrate for peroxidase. Those bacteria containing peroxidase-bearing plasmid will produce colonies surrounded by a halo of clear agar, due to digestion of the substrate by secreted peroxidase.

Alternatively, the DNA sequence encoding the enzyme may be prepared synthetically by established standard methods, e.g. the phosphoamidite method described by S. L. Beaucage and M. H. Caruthers, *Tetrahedron Letters* 22, 1981, pp. 1859–1869, or the method described by Matthes et al., *The EMBO J.* 3, 1984, pp. 801–805. According to the phosphoamidite method, oligonucleotides are synthesized, e.g. in an automatic DNA synthesizer, purified, annealed, ligated and cloned in appropriate vectors.

Finally, the DNA sequence may be of mixed genomic and synthetic, mixed synthetic and cDNA or mixed genomic and cDNA origin prepared by ligating fragments of synthetic, genomic or cDNA origin (as appropriate), the fragments corresponding to various parts of the entire DNA sequence, in accordance with standard techniques. The DNA sequence may also be prepared by polymerase chain reaction (PCR) using specific primers, for instance as described in U.S. Pat. No. 4,683,202 or R. K. Saiki et al., *Science* 239, 1988, pp. 487–491.

Once a peroxidase-encoding DNA sequence has been isolated, and desirable sites for mutation identified, mutations may be introduced using synthetic oligonucleotides. These oligonucleotides contain nucleotide sequences flanking the desired mutation sites; mutant nucleotides are inserted during oligonucleotide synthesis. In a specific method, a single-stranded gap of DNA, bridging the peroxidase-encoding sequence, is created in a vector carrying the peroxidase gene. Then the synthetic nucleotide, bearing the desired mutation, is annealed to a homologous portion of the single-stranded DNA. The remaining gap is then filled in with DNA polymerase I (Klenow fragment) and the construct is ligated using T4 ligase. A specific example of this method is described in Morinaga et al., (1984, Biotechnology 2:646–639). U.S. Pat. No. 4,760,025, by Estell et al., issued Jul. 26, 1988, discloses the introduction of oligonucleotides encoding multiple mutations by performing minor alterations of the cassette, however, an even greater variety of mutations can be introduced at any one time by the Morinaga method, because a multitude of oligonucleotides, of various lengths, can be introduced.

Another method of introducing mutations into peroxidase-encoding sequences is described in Nelson and Long, *Analytical Biochemistry* 180, 1989, pp. 147–151. It involves the 3-step generation of a PCR fragment containing the desired mutation introduced by using a chemically synthesized DNA strand as one of the primers in the PCR reactions. From the PCR-generated fragment, a DNA fragment carrying the mutation may be isolated by cleavage with restriction endonucleases and reinserted into an expression plasmid.

According to the invention, a mutated peroxidase-coding sequence produced by one of the methods described above, or any alternative methods known in the art, can be expressed, in enzyme form, using an expression vector which typically includes control sequences encoding a promoter, operator, ribosome binding site, translation initiation signal, and, optionally, a repressor gene or various activator genes. To permit the secretion of the expressed protein, nucleotides encoding a signal sequence may be inserted prior to the peroxidase-coding sequence. For expression under the direction of control sequences, a target gene is operably linked to the control sequences in the proper reading frame. Promoter sequences that can be incorporated into plasmid vectors, and which can support the transcription of the mutant peroxidase gene, include but are not limited to the prokaryotic β-lactamase promoter (Villa-Kamaroff, et al., 1978, Proc. Natl. Acad. Sci. U.S.A. 75:3727–3731) and the tac promoter (DeBoer, et al., 1983, Proc. Natl. Acad. Sci. U.S.A. 80:21–25). Further references can also be found in "Useful proteins from recombinant bacteria" in Scientific American, 1980, 242:74–94.

According to one embodiment *B. subtilis* is transformed by an expression vector carrying the mutated DNA. If expression is to take place in a secreting microorganism such as *B. subtilis* a signal sequence may follow the translation initiation signal and precede the DNA sequence of interest. The signal sequence acts to transport the expression product to the cell wall where it is cleaved from the product upon secretion. The term "control sequences" as defined above is intended to include a signal sequence, when present.

The host organism transformed with the DNA sequence encoding the peroxidase variant of the invention may also be a yeast, preferably a strain of Saccharomyces, e.g. *Saccharomyces cerevisiae* or *Schizosaccharomyces pombe*, or Pichia, e.g. *Pichia pastoris*.

In a currently preferred method of producing the peroxidase variant of the invention, a filamentous fungus is used as the host organism. The filamentous fungus host organism may conveniently be one which has previously been used as a host for producing recombinant proteins, e.g. a strain of Aspergillus sp., such as *A. niger, A. nidulans* or *A. oryzae*. The use of *A. oryzae* in the production of recombinant proteins is extensively described in, e.g. EP 238 023.

For expression of peroxidase variants in Aspergillus, the DNA sequence coding for the peroxidase variant is preceded by a promoter. The promoter may be any DNA sequence exhibiting a strong transcriptional activity in Aspergillus and may be derived from a gene encoding an extracellular or intracellular protein such as an amylase, a glucoamylase, a protease, a lipase, a peroxidase, a cellulase or a glycolytic enzyme.

Examples of suitable promoters are those derived from the gene encoding *A. oryzae* TAKA amylase, *Rhizomucor miehei* aspartic proteinase, *A. niger* neutral α-amylase, *A. niger* acid stable α-amylase, *A. niger* glucoamylase, *Rhizomucor miehei* lipase, *A. oryzae* alkaline protease or *A. oryzae* triose phosphate isomerase.

In particular when the host organism is *A. oryzae*, a preferred promoter for use in the process of the present invention is the *A. oryzae* TAKA amylase promoter as it exhibits a strong transcriptional activity in *A. oryzae*. The sequence of the TAKA amylase promoter appears from EP 238 023.

Termination and polyadenylation sequences may suitably be derived from the same sources as the promoter.

The techniques used to transform a fungal host cell may suitably be as described in EP 238 023.

To ensure secretion of the peroxidase variant from the host cell, the DNA sequence encoding the peroxidase variant may be preceded by a signal sequence which may be a naturally occurring signal sequence or a functional part thereof or a synthetic sequence providing secretion of the protein from the cell. In particular, the signal sequence may be derived from a gene encoding an Aspergillus sp. amylase or glucoamylase, a gene encoding a *Rhizomucor miehei* lipase or protease, or a gene encoding a Humicola cellulase, xylanase or lipase. The signal sequence is preferably derived from the gene encoding *A. oryzae* TAKA amylase, *A. niger* neutral α-amylase, *A. niger* acid-stable α-amylase, *Coprinus cinereus* or macrorhizus peroxidase, or *A. niger* glucoamylase.

The medium used to culture the transformed host cells may be any conventional medium suitable for growing Aspergillus cells. The transformants are usually stable and may be cultured in the absence of selection pressure. However, if the transformants are found to be unstable, a selection marker introduced into the cells may be used for selection.

The mature peroxidase protein secreted from the host cells may conveniently be recovered from the culture medium by well-known procedures including separating the cells from the medium by centrifugation or filtration, and precipitating proteinaceous components of the medium by means of a salt such as ammonium sulphate, followed by chromatographic procedures such as ion exchange chromatography, affinity chromatography, or the like.

To obtain an optimal bleaching effect of the peroxidase variant, hydrogen peroxide or a precursor of hydrogen peroxide, preferably perborate or percarbonate, may advantageously be added to the bleaching agent of the invention as the substrate for the peroxidase variant.

While the mechanism governing the ability of peroxidase to effect bleaching of coloured substances present on fabrics or in solution has not yet been elucidated, it is currently believed that the enzyme acts by reducing hydrogen peroxide or molecular oxygen and oxidizing the coloured substance (donor substrate) dissolved or dispersed in the wash liquor, thereby either generating a colourless substance or providing a substance which is not adsorbed to the fabric. This reaction is shown in Reaction Scheme 1 below
Reaction Scheme 1:

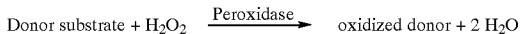

By using a peroxidase variant according to the invention which is less sensitive to hydrogen peroxide, it may be possible to add a smaller amount of the enzyme to the bleaching/washing liquor and yet obtain a satisfactory bleaching effect.

In the bleaching agent, the amount of hydrogen peroxide or hydrogen peroxide precursor preferably corresponds to a hydrogen peroxide concentration in the wash liquor of between 10 $\mu$M and 20 mM.

For use of the present peroxidase variant as a bleaching agent, it has surprisingly been found that the addition of another oxidisable substrate (for the peroxidase variant of the invention) at the beginning or during the washing and/or rinsing process may enhance the bleaching effect of the peroxidase variant employed. This is thought to be ascribable to the formation of short-lived radicals or other oxidised states of this substrate which participate in the bleaching or other modification of the coloured substance. Examples of such oxidisable substrates are organic compounds such as phenolic compounds, e.g. 7-hydroxycoumarin, vanillin, p-hydroxycinnamic acid, p-hydroxybenzene sulphonate or 2,4-dichlorophenol. Other examples of phenolic compounds which may be used for the present purpose are those given in M. Kato and S. Shimizu, *Plant Cell Physiol.* 26(7), 1985, pp. 1291–1301 (cf. Table 1 in particular) or B. C. Saunders et al., Peroxidase, London, 1964, p. 141 ff. The amount of oxidisable substrate to be added is suitably between about 1 $\mu$M and 1 mM.

According to the invention, the peroxidase variant may typically be added as a component of a detergent composition. As such, it may be included in the detergent composition in the form of a non-dusting granulate, a liquid, in particular a stabilized liquid, or a protected enzyme. Non-dusting granulates may be produced, e.g., as disclosed in U.S. Pat. Nos. 4,106,991 and 4,661,452 (both to Novo Industri A/S) and may optionally be coated by methods known in the art. Liquid enzyme preparations may, for instance, be stabilized by adding a polyol such as propylene glycol, a sugar or sugar alcohol, lactic acid or boric acid according to established methods. Other enzyme stabilizers are well known in the art. Protected enzymes may be prepared according to the method disclosed in EP 238,216. The detergent composition may also comprise one or more substrates for the enzyme.

The detergent composition of the invention may be in any convenient form, e.g. as powder, granules or liquid. A liquid detergent may be aqueous, typically containing up to 70% water and 0–20% organic solvent.

The detergent composition comprises a surfactant which may be anionic, non-ionic, cationic, amphoteric or a mixture of these types. The detergent will usually contain 5–30% anionic surfactant such as linear alkyl benzene sulphonate (LAS), alpha-olefin sulphonate (AOS), alkyl sulphate (AS), alcohol ethoxy sulphate (AES) or soap. It may also contain 3–20% non-ionic surfactant such as nonyl phenol ethoxylate or alcohol ethoxylate.

The detergent composition may additionally comprise one or more other enzymes, such as an amylase, lipase, cellulase or protease.

The pH (measured in aqueous detergent solution) will usually be neutral or alkaline, e.g. 7–11. The detergent may contain 1–40% of a detergent builder such as zeolite, phosphate, phosphonate, citrate, NTA, EDTA or DTPA, alkenyl succinic anhydride, or silicate, or it may be unbuilt (i.e. essentially free of a detergent builder). It may also contain other conventional detergent ingredients, e.g. fabric conditioners, foam boosters, anti-corrosion agents, soil-suspending agents, sequestering agents, anti-soil redeposition agents, stabilizing agents for the enzyme(s), foam depressors, dyes, bactericides, optical brighteners or perfumes.

Particular forms of detergent composition within the scope of the invention include:

a) A detergent composition formulated as a detergent powder containing phosphate builder, anionic surfactant, nonionic surfactant, silicate, alkali to adjust to desired pH in use, and neutral inorganic salt.

b) A detergent composition formulated as a detergent powder containing zeolite builder, anionic surfactant, nonionic surfactant, acrylic or equivalent polymer, silicate, alkali to adjust to desired pH in use, and neutral inorganic salt.

c) A detergent composition formulated as an aqueous detergent liquid comprising anionic surfactant, nonionic surfactant, humectant, organic acid, alkali, with a pH in use adjusted to a value between 7 and 10.5.

d) A detergent composition formulated as a non-aqueous detergent liquid comprising a liquid nonionic surfactant consisting essentially of linear alkoxylated primary alcohol, phosphate builder, alkali, with a pH in use adjusted to a value between about 7 and 10.5.

e) A detergent composition formulated as a detergent powder in the form of a granulate having a bulk density of at least 600 g/l, containing anionic surfactant and nonionic surfactant, low or substantially zero neutral inorganic salt, phosphate builder, and sodium silicate.

f) A detergent composition formulated as a detergent powder in the form of a granulate having a bulk density of at least 600 g/l, containing anionic surfactant and nonionic surfactant, low or substantially zero neutral inorganic salt, zeolite builder, and sodium silicate.

g) A detergent composition formulated as a detergent powder containing anionic surfactant, nonionic surfactant, acrylic polymer, fatty acid soap, sodium carbonate, sodium sulphate, clay particles, and sodium silicate.

h) A liquid compact detergent comprising 5–65% by weight of surfactant, 0–50% by weight of builder, and 0–30% by weight of electrolyte.

Apart from these ingredients, the detergent compositions a)–h) include a peroxidase variant of the invention and a substrate therefor, and optionally one or more other enzymes, as indicated above. Liquid detergents preferably include stabilised hydrogen peroxide precursors.

It is at present contemplated that, in the detergent composition of the invention, the peroxidase variant may be added in an amount corresponding to 0.01–100 mg enzyme per liter of wash liquor.

The present invention is further illustrated in the following examples which are not in any way intended to limit the scope of the invention as claimed.

EXAMPLE 1

Construction of a Plasmid Expressing the N142S Variant of *Coprinus cinereus* Peroxidase 1. Cloning of cDNA Encoding a *Coprinus cinereus* Peroxidase Construction of a Probe by PCR Peroxidase cDNA fragments were prepared by polymerase chain reaction (PCR) using specific oligonucleotide primers (R. K. Saiki et al., *Science* 239, 1988, pp. 487–491) constructed on the basis of the amino acid sequence of the Coprinus macrorhizus peroxidase. PCR was carried out using the Gene Amp kit and apparatus (available from Perkin Elmer Cetus, Norwalk, Conn., USA) in accordance with the manufacturer's instructions, with the exception that the reaction was conducted at 28° C. for the first three cycles in order to obtain better hybridisation to the first strand cDNA (prepared from mRNA obtained from *Coprinus cinereus*, IFO 8371) and subsequently at 65° C. for 30 cycles of PCR.

The following specific primers were used for PCR:

```
                    T  T
1.  5'-GCGCGAATTCGTNGGNATNAACCACGG-3'       (SEQ ID NO:3)

A  A
2.  3'-TACAGNTTGACGGGNGGCCTAGGCG-5'         (SEQ ID NO:4)

A     T T
3.  5'-GCGAATTCACNCCNCAGGTNTTCGACAC-3'      (SEQ ID NO:5)

A     T A
4.  3'-GGNAAGGGNCCNCTCAAGCCTAGGCG-5'        (SEQ ID NO:6)

A
5.  5'-GCGCGAATTCTGGCAGTCNAC-3'             (SEQ ID NO:7)

A
6.  5'-GCGCGAATTCTGGCAGAGNATG-3'            (SEQ ID NO:8)

T
7.  3'-CGNTACCGNTTCTACAGCCTAGG-5'           (SEQ ID NO:9)
```

"N" denoting a mixture of all four nucleotides.

The primers were combined as follows: 1 with 2, 3 with 4, 5 with 7, 6 with 7, 1 with 4, 1 with 7 and 3 with 7. The PCR fragments were thus extended with an EcoRI site at the 5'-end and a BamHI site at the 3'-end. The PCR reactions were analysed on a 1% agarose gel. Bands of the expected size were found in all reactions. To verify that the bands corresponded to peroxidase-specific sequences, the gel was subjected to Southern blotting and hybridised to an oligonucleotide probe with the following sequence

```
        T A A A T
   5'-GTCTCGATGTAGAACTG-3'     (SEQ ID NO:10)
        T
``` which is positioned between PCR primers 3 and 4. The probe was found to hybridise to bands of approximately 130 bp, 420 bp, 540 bp and 240 bp, thus confirming that the DNA bands observed correspond to peroxidase sequences.

DNA from the various PCR reactions was digested with EcoRI and BamHI and cloned into the plasmid pUC19 (C. Yanisch-Perron et al., *Gene* 33, 1985, pp. 103–119). Colonies containing the correct PCR fragments were identified by hybridisation using the oligonucleotide probe specified above. DNA from positive colonies was analysed by restriction enzyme mapping and partial DNA sequence analysis as described by Sanger et al., *Proc. Natl. Acad. Sci. USA* 74, 1977, pp. 5463–5467. A 430 bp fragment from one of the clones, obtained by using primer 1 and 4, was used to screen a *Coprinus cinereus* cDNA library as described below.

Construction of a *Coprinus cinereus* cDNA Library in *E. coli*

Total RNA was extracted from homogenized *Coprinus cinereus* (IFO 8371) mycelium, collected at the time for maximum activity of the peroxidase by methods as described by Boel et al. (EMBO J., 3: 1097–1102, 1984) and Chirgwin et al. (Biochemistry (Wash), 18: 5294–5299, 1979). Poly(A)-containing RNA is obtained by two cycles of affinity chromatography on oligo(dT)-cellulose as described by Aviv and Leder (PNAS, USA 69:1408–1412, 1972). cDNA is synthesized by means of a cDNA synthesis kit from Invitrogen according to the manufacturer's instructions. About 50.000 *E. coli* recombinants from the *Coprinus cinereus* cDNA library were transferred to Whatman 540 paper filters. The colonies were lysed and immobilized as described by Gergen et al. (Nucleic Acids Res. 7, 2115–2135, 1979). The filters were hybridized with the $^{32}$P-labelled 430 bp peroxidase-specific probe in 0.2×SSC, 0.1% SDS. Hybridization and washing of the filters was conducted at 65° C. followed by autoradiography for 24 hours with an intensifier screen. After autoradiography, the filters were washed at increasing temperatures followed by autoradiography for 24 hours with an intensifier screen. In this way, more than 50 positive clones were identified. Miniprep plasmid DNA was isolated from hybridizing colonies by standard procedures (Birnboim and Doly Nucleic Acids Res. 7, 1513–1523, 1979), and the DNA sequence of the cDNA insert was determined by the Sanger dideoxy procedure (Sanger et al., *Proc. Natl. Acad. Sci. USA* 74, 1977, pp. 5463–5467). The peroxidase cDNA fragment was excised from the vector by cleavage with HindIII/XhoI and was purified by agarose gel electrophoresis, electroeluted and made ready for ligation reactions. The cDNA fragment was ligated to HindIII/XhoI digested pHD414 to generate pCiP in which the cDNA is under transcriptional control of the TAKA promotor from *Asperaillus oryzae* and the AMG terminator from *Aspergillus niger*.

Construction of the Aspergillus Expression Vector pHD414

The vector pHD414 is a derivative of the plasmid p775 (described in EP 238 023). In contrast to p775, pHD414 has a string of unique restriction sites between the promotor and the terminator.

The plasmid was constructed by removal of an approximately 200 bp long fragment (containing undesirable restriction sites) at the 3' end of the terminator, and subsequent removal of an approximately 250 bp long fragment at the 5' end of the promoter, also containing undesirable restriction sites. The 200 bp region was removed from p775 by cleavage with NarI (positioned in the pUC vector) and XbaI (positioned just 3' to the terminator), subsequent filling in the generated ends with Klenow DNA polymerase+dNTP, purification of the vector fragment on gel and religation of the vector fragment. The DNA was transformed into *E. coli* MC1061 as described above. 10 colonies (pHD413-1 to -10) were selected and analyzed by restriction enzyme analysis. One of the clones exhibiting the expected band pattern in the restriction enzyme analysis was used in the construction of pHD414.

pHD413 was cut with StuI (positioned in the 5' end of the promoter) and PvuII (positioned in the pUC vector) and fractionated on a gel. The vector fragment was purified, religated and transformed into *E. coli* MC1061. 12 colonies were selected and analyzed by restriction enzyme analysis. All 12 clones exhibited the expected band pattern. The plasmid pHD414 is shown in FIG. 1.

2. 3-step PCR mutagenesis:
3-step mutagenisation involves the use of four primers:
Mutagenisation primer (=A): 5'-CAG GAG TTC CCA ACC-3'(SEQ ID NO: 11)

```
PCR Helper 1 (=B):                        (SEQ ID NO:12)
5'-TGA TCA TAG TAC CAT CTA ATT ACA TCA AGC GGC-3'

PCR Helper 2 (=C):                        (SEQ ID NO:13)
5'-CTG TAA TAC GAC TCA CTA-3'

PCR Handle (=D):                          (SEQ ID NO:14)
5'-TGA TCA GAC TAG TAC CAT-3'
```

Primer A and B were diluted to 20 pmol/µl. Primer C and D were diluted to 100 pmol/µl.

All 3 steps were carried out in a 10×PCR buffer containing: 100 mM Tris-HCl, pH 8.3, 500 mM KCl, 15 mM MgCl$_2$, 0.1% gelatin, 200 µl of each of 2 mM dATP, 2 mM dCTP, 2 mM dGTP, 2 mM TTP, and 200 µl of H$_2$O.

In step 1, a reaction mixture composed of 10 µl of 10×PCR buffer, 50 µl of 2×nucleotide solution, 5 µl of primer A, 5 µl of primer B, 1 µl of pCiP (0.05 µg/µl), 30 µl of H$_2$O, 0.5 µl of Taq polymerase, and 80 µl of paraffin, was run through 1 cycle consisting of 2 minutes at 94° C., 15 cycles consisting of 1 minute at 94° C., 1 minute at 50° C. and 2 minutes at 72° C., 15 cycles consisting of 1 minute at 94° C., 1 minute at 50° C. and 3 minutes at 72° C., and 1 cycle consisting of 5 minutes at 72° C.

10 µl of the PCR product was purified on an agarose gel and redissolved in 10 µl of H$_2$O. Then, step 2 was carried out. A reaction mixture composed of 10 µl of 10×PCR buffer, 50 µl of 2×nucleotide solution, 5 µl of the purified product of step 1, 1 µl pCiP (0.05 µg/µl), 30 µl of H$_2$O, 0.5 µl of Taq polymerase, and 80 µl of paraffin, was run through 1 cycle consisting of 5 minutes at 94° C., 2 minutes at 50° C. and 10 minutes at 72° C.

To the step 2 reaction mixture, 1 µl of primer C and 1 µl of primer D were added. The PCR reaction was carried out as described for step 1.

3. Isolation of the Mutated Restriction Fragment:

The product from step 3 was isolated from an agarose gel and re-dissolved in 20 µl H$_2$O. Then, it was digested with the restriction enzymes XbaI and KpnI in NEBuffer 2 (New England Biolabs) supplemented with bovine serum albumin (BSA) in a total volume of 20 µl at 37° C. overnight. The 570 bp XbaI/KpnI fragment was isolated from an agarose gel.

4. Ligation to Expression Vector pCiP:

The expression plasmid pCiP was cleaved with XbaI and KpnI under the conditions indicated above and the large fragment was isolated from an agarose gel. To this vector, the mutated fragment isolated above was ligated and the ligation mixture was used to transform *E. coli*. The presence and orientation of the fragment was verified by cleavage of a plasmid preparation from a transformant with restriction enzymes. Sequence analysis was carried out on the double-stranded plasmid using the di-deoxy chain termination procedure developed by Sanger. The resulting plasmid is identical to pCiP except for the altered codon.

EXAMPLE 2

Construction of Plasmids Expressing other Variants of *Coprinus peroxidase*

The following mutants were constructed using the same method as described in Example 1, except that other restriction enzymes were used for digesting the PCR-product and the vector used for recloning the mutated fragment. Mutations and primers used for the modifications are listed below.

| Mutation | Primer A sequence | |
|---|---|---|
| N142T | 5'-CAG GAG CAC TAG TTC CCA ACC C-3' | (SEQ ID NO:15) |
| D56N | 5'-TTT TCC ATA ACG CGA TCG-3' | (SEQ ID NO:16) |
| G156F | 5'-GGT CCC TTT AAC ACT GTC-3' | (SEQ ID NO:17) |
| N142P | 5'-CAG GAG CCC GAG TTC CCA AC-3' | (SEQ ID NO:18) |
| N142D | 5'-CAG GAG CGA CTC TTC CCA AC-3' | (SEQ ID NO:19) |
| G154E+ G156F+ N157E | 5'-GAT CCC CGA GCC CTT CGA AAC TGT CAC T-3' | (SEQ ID NO:20) |
| G154E+ G156F | 5'-GAT CCC CGA GCC CTT TAA CAC TGT C-3' | (SEQ ID NO:21) |
| G156F+ N157F | 5'-GGT CCC TTC ACT GTC ACT GC -3' | (SEQ ID NO:22) |
| N157F | 5'-TCC CGG ATT TAC TGT CAC TGC-3' | (SEQ ID NO:23) |
| D56T | 5'-GTT TTC CAT ACT GCG ATC GG-3' | (SEQ ID NO:24) |
| D56I | 5'-GTT TTC CAT ATT GCG ATC GG-3' | (SEQ ID NO:25) |
| D245I | 5'-ATG AGG TCG ATC GCT CTC TT-3' | (SEQ ID NO:26) |
| D245T | 5'-ATG AGG TCC ACG GCT CTC TT-3' | (SEQ ID NO:27) |
| D245N | 5'-ATG AGG TCC AAT GCT CTC TT-3' | (SEQ ID NO:28) |
| C22S | 5'-AAC AGC CAG AGC TGC GTC T-3' | (SEQ ID NO:29) |
| C23S | 5'-AGC CAG TGC AGC GTC TGG TT-3' | (SEQ ID NO:30) |
| Q1S | 5'-GCT CTA CCC TCC GGA CCT GGA-3' | (SEQ ID NO:31) |
| Q1E | 5'-GCT CTA CCC GAG GGT CCT GGA-3' | (SEQ ID NO:32) |
| A304 STOP | 5'-AAC AAC TGA GCT CCT GTT-3' | (SEQ ID NO:33) |
| C256S | 5'-ACC GCC TCG CGA TGG CAA-3' | (SEQ ID NO:34) |
| G154E | 5'-TTG ATC CCC GAG CCC GGA AAC-3' | (SEQ ID NO:35) |
| N157E | 5'-GGT CCC GGA GAA ACT GTC ACT-3' | (SEQ ID NO:36) |
| T331A+ S338A | 5'-ATT GCT GCA GCC TCA GGC CCT CTC CCA GCG CTC GCT CCT-3' | (SEQ ID NO:37) |
| T331N+ S383A | 5'-ATT GCT AAT GCC TCA GGC CCT CTC CCA GCG CTC GCT CCT-3' | (SEQ ID NO:38) |

-continued

| Mutation | Primer A sequence | |
|---|---|---|
| S8N | 5'-GGG GCA CGT GAC GTT CCC GCC-3' | (SEQ ID NO:39) |
| S263N+ N265S | 5'-CAT AAC TTC GCT GCT ATT GGT CAT -3' | (SEQ ID NO:40) |
| Q38N | 5'-CTT GGA CCC ATT GTA GTT-3' | (SEQ ID NO:41) |
| A304S | 5'-AAC AGG AGC GCT GTT GTT GGA-3' | (SEQ ID NO:42) |
| P-1+ QIE | 5'-CTC GCT CTA ATG GAG GGT CCT-3' | (SEQ ID NO:43) |

It should be noted that variants in position 1–29 were digested with BamHI and XbaI in NEBuffer 3 (New England Biolabs) supplemented with BSA, resulting in a 160 bp fragment. Variants in position 30–219 were digested with XbaI/KpnI in NEBuffer 2 supplemeted with BSA, resulting in a 570 bp fragment. Variants in position 220–277 were digested with KpnI/MscI in NEBuffer 2 suplemented with BSA, resulting in a 170 bp fragment. Variants in position 278–363 were digested
with MscI/XhoI in NEBuffer 2 supplemented with BSA, resulting in a 420 bp fragment.

EXAMPLE 3

Expression of Coprinus peroxidase Variants in Aspergillus oryzae

Transformation of Aspergillus oryzae or Aspergillus niger (general procedure)

100 ml of YPD medium (Sherman et al., Methods in Yeast Genetics, Cold Spring Harbor Laboratory, 1981) was inoculated with spores of A. oryzae or A. niger and incubated with shaking at 37° C. overnight. The mycelium was harvested by filtration through miracloth and washed with 200 ml of 0.6 M MgSO$_4$. The mycelium was suspended in 15 ml of 1.2 M MgSO$_4$. 10 mM NaH$_2$PO$_4$, pH=5.8. The suspension was cooled on ice, and 1 ml of buffer containing 120 mg of Novozym® 234, batch 1687 was added. After 5 minutes 1 ml of 12 mg/ml BSA (Sigma type H25) was added, and incubation with gentle agitation was continued for 1.5–2.5 hours at 37° C. until a large number of protoplasts was visible in a sample inspected under the microscope.

The suspension was filtered through miracloth, the filtrate was transferred to a sterile tube and overlayered with 5 ml of 0.6 M sorbitol, 100 mM Tris-HCl, pH=7.0. Centrifugation was performed for 15 minutes at 100×g, and protoplasts were collected from the top of the MgSO$_4$ cushion. 2 volumes of STC (1.2 M sorbitol, 10 mM Tris-HCl, pH=7.5. 10 mM CaCl$_2$) were added to the protoplast suspension and the mixture was centrifuged for 5 minutes at 1000×g. The protoplast pellet was resuspended in 3 ml of STC and repelleted. This procedure was repeated. Finally the protoplasts were resuspended in 0.2–1 ml of STC.

100 µl of the protoplast suspension was mixed with 5–25 µg of the appropriate DNA in 10 µl of STC. Protoplasts from the A1560 strain of A. oryzae (IFO 4177) were mixed with pToC186 (an A. nidulans amdS gene carrying plasmid). The mixture was left at room temperature for 25 minutes. 0.2 ml of 60% PEG 4000 (BDH 29576), 10 mM CaCl$_2$ and 10 mM Tris-HCl, pH=7.5, were added and carefully mixed (twice) and finally 0.85 ml of the same solution was added and carefully mixed. The mixture was left at room temperature for 25 minutes, spun at 2500×g for 15 minutes and the pellet was resuspended in 2 ml of 1.2 M sorbitol. After another sedimentation, the protoplasts were spread on the appropriate plates. Protoplasts from the A1560 strain transformed with pToC186 were spread on minimal plates (Cove Biochem. Biophys. Acta 113 (1966) 51–56) containing 1.0 M sucrose, pH=7.0, 10 mM acetamide as nitrogen source and 20 mM CsCl to inhibit background growth. After incubation for 4–7 days at 37° C. spores were picked, suspended in sterile water and spread for single colonies. This procedure was repeated and spores of a single colony after the second reisolation were stored as defined transformants.

Production of Recombinant Coprinus cinereus peroxidase Variants in an A. oryzae Strain Plasmids containing the appropriate mutations in the peroxidase gene were transformed into A. oryzae A1560 by cotransformation with pToC186 containing the amds gene from A. nidulans as described above with a mixture of equal amounts of pCiP and pToC186 (approximately 5 µg of each). Transformants which were able to use acetamide as their sole nitrogen source were reisolated twice. After growth on YPD medium (Sherman et al. 1981) for three days culture supernatants were analysed by a peroxidase activity assay using ABTS (vide below). The best transformants were selected for further studies.

EXAMPLE 4

Hydrogen Peroxide Stability and Substrate Activity of Coprinus peroxidase Variants of the Invention Wild-type recombinant Coprinus cinereus peroxidase (rCiP) and the variants G156F, N157F, G154E+G156F+ N157E, G154E+G156F, D245T, and D245N, prepared as described above, were tested for their ability to oxidise the substrates 2,2'-azino-di-[3-ethylbenzthiazoline-6-sulfonic acid], diammonium salt (ABTS), Methyl Orange (MO), vanillin (3-methoxy-4-hydroxybenzaldehyde) (Van), 2-aminobenzoic acid (AMB), veratryl alcohol (Ver) and Mn$^{++}$. Samples of the tested variants were pure and supplied in elution buffer. The enzyme concentration was determined from $A_{405}$ and $\epsilon_{405}$=109 mM$^-$. Enzyme stock dilutions used in assays were stable, leading to reproducible oxidation rates.

Assay conditions were substantially as described by Andersen et al. in Biochemical, Molecular and Physiological Aspects of Plant Peroxidases (J. Lobarzewski, H. Greppin, C. Penel and T. Gaspar, Eds.) 1991, pp. 169–175, as outlined in Table 1 below.

TABLE 1

| | rCiP Assays | |
|---|---|---|
| Substrate | Conditions 25° C. | Velocity mabs/min |
| MO | pH = 7.0 465 nm [MO] = 46 µM [H$_2$O$_2$] = 200 µM [rCiP] = 49 nM | 215 ± 5 0 – 120 s |
| ABTS | pH = 7.0 418 nm [ABTS] = 1.7 mM [H$_2$O$_2$] = 1.0 mM [rCiP] = 50 pM | 163 ± 1 0 – 120 s |
| Van | pH = 7.0 349 nm [Van] = 176 µM [H$_2$O$_2$] = 232 µM [rCiP] = 1.1 nM | 419 ± 10 0 – 80 s |

TABLE 1-continued rCiP Assays

| Substrate | Conditions 25° C. | Velocity mabs/min |
|---|---|---|
| AMB | pH = 7.0 310 nm<br>[AMB] = 100 $\mu$M<br>[$H_2O_2$] = 100 $\mu$M<br>[rCiP] = 11 nM | 40 ± 2<br><br><br>0 – 100 s |
| Ver | pH = 3.5 310 nm<br>[Ver] = 130 $\mu$M<br>[$H_2O_2$] = 230 $\mu$M<br>[LiP] = 500 nM | 31 ± 5<br><br><br>0 – 200 s |
| $Mn^{2+}$ | pH = 5.0 300 nm<br>[$Mn^{2+}$] = 120 $\mu$M<br>[Lac] = 50 mM<br>[$H_2O_2$] = 35 $\mu$M<br>[MnP] = 11 nM | 21 ± 5<br><br><br><br>50 – 200 s |
| $H_2O_2$ | pH 7.0 420 nm<br>[$H_2O_2$] = 4.4 mM<br>[rCiP] = 5.5 $\mu$M | $t_{1/2}$ = 14 min |

Hydrogen peroxide stability was measured as the irreversible inactivation of CiP-III (formed in excess of hydrogen peroxide, cf. M. B. Andersen et al., *Acta Chim. Scand.* 45, 1991, pp. 1080–1086). The absorbance at 405 nm was measured over time, and the time required to decrease the absorbance at 405 nm to half the original value is defined as the half-life. The test solution was composed of 10 mM sodium phosphate buffer, pH 7, 5.5 $\mu$M *Coprinus cinereus* peroxidase, 4.4 mM (or 800 times molar excess) of hydrogen peroxide, measured at 25° C.

It appears from Table 2 below that none of the peroxidase variants exhibited increased activity compared to wild-type rCiP. One variant retained wild-type activity, while the other variants exhibited decreased activity. The variant G154E+G156F+N157E had a decreased activity level by about a factor 2. The active site variants (D245N and D245T) exhibited the most pronounced changes in activity and substrate specificity. The variants G154F and N157E retained wild-type stability, while the variants G154E+G156F+N157E and G154E+G156F had a four times increased stability. D245N had a decreased half-life, while D245T had a half-life of about an hour.

the assay described in Example 4, was tested for its ability to bleach dyes in the presence of different accelerators. Wild-type rCiP was used as control. The enzyme concentration was determined from $A_{405}$ and $\epsilon_{405}$=109 $mM^{-1}$ to be 233 $\mu$M for the variant and 110 $\mu$M for the wild-type rCiP.

Wild-type rCiP and the G154E+G156F+N157E variant were assayed for dye bleaching under the following conditions:

The test solution was composed of 10 mM sodium phosphate buffer, pH 8, 200 $\mu$M hydrogen peroxide, 50 $\mu$M oxidisable substrate and 10 nM rCiP or peroxidase variant. The dyes used in the assay were Methyl Orange, Direct Blue 1 and 90 and Acid Red 151. The concentration of dye was about 4 $\mu$M. The test temperature was 25° C. The oxidisable substrates were p-hydroxybenzene sulphonate, vanillin, 7-hydroxycoumarin and 4-hydroxycinnamic acid, commonly used as bleach accelerators.

The bleaching affect was monitored over about 15 minutes as the change in absorbance measured at 465 nm for Methyl Orange, 600 nm for Direct Blue 1, 610 nm for Direct Blue 90 and 510 nm for Acid Red 151. In the presence of 7-hydroxycoumarin, Methyl Orange was bleached to the same level of absorbance by the wild-type and variant peroxidase. The presence of vanillin gave rise to a slight bleaching effect for the variant, while the other two accelerators did not have any effect on bleaching. In the presence of 7-hydroxycoumarin, Direct Blue 90 was bleached to the same level of absorbance by the two enzymes, the presence of vanillin gave rise to a slight bleaching effect for the variant, and the other two accelerators had no effect. Direct Blue 1 was bleached completely by the wild-type peroxidase in the presence of all four accelerators, while the peroxidase variant was able to bleach the dye in the presence of 7-hydroxycoumarin and vanillin, and partly in, the presence of 4-hydroxycinnamic acid, whereas p-hydroxybenzene sulphonate had no effect. In the presence of 7-hydroxycoumaric acid, Acid Red 151 was bleached completely by the peroxidase variant at approximately the same rate and overall performance as by the wild-type enzyme, while the other two accelerators had no effect.

Based on these results, it is concluded that the peroxidase variant G154E+G156F+N157E bleaches each of the four dyes as efficiently as the wild-type enzyme in the presence of 7-hydroxycoumarin as accelerator. In the presence of

TABLE 2 rCiP mutants
Substrate oxidation, mabs/min

| CiP | Stock solution $\mu$M | MO | ABTS | Van | AMB | Ver | $Mn^{2+}$ | $t_{1/2}$ min |
|---|---|---|---|---|---|---|---|---|
| rCiP | 112 | 215 ± 5 | 163 ± 1 | 419 ± 10 | 40 ± 2 | 0 | 0 | 14 |
| G156F | 140 | 212 ± 2 | 134 ± 1 | 437 ± 2 | 42 ± 1 | 0 | 0 | 20 |
| N157F | 34 | 117 ± 0 | 83 ± 1 | 343 ± 4 | 27 ± 1 | 0 | 0 | 18 |
| G154E G156F G157E | 233 | 46 ± 1 | 38 ± 2 | 39 ± 1 | 0 | 0 | 0 | 55 |
| G154E G156F | 25 | 25 ± 2 | 15 ± 1 | 31 ± 2 | 0 | 0 | 0 | 55 |
| D245T | 23 | 10 ± 0 | 5 ± 1 | 0 | 0 | 0 | 0 | ~60 |
| D245N | 60 | 5 ± 0 | 24 ± 2 | 0 | 0 | 0 | 0 | 6 |

EXAMPLE 5
Bleaching Effect of a Peroxidase Variant of the Invention

A peroxidase variant of the invention, G154E+G156F+N157E, which exhibited favourable stability properties in vanillin, the variant bleaches two of the dyes completely. The variant is unable to bleach any of the four dyes in the absence of accelerator. This may be explained by the location of the mutations introduced into the variant. They are located on the protein surface near the substrate channel, making it less accessible to large molecules such as dyes.

EXAMPLE 6
Reactions With ABTS

Purified CiP and variants produced as described in Example 2 were stored in 3 M ammonium sulfate at 4° C. The 3 M ammonium sulfate supernatant was decanted after centrifugation, and the precipitate was solubilized in 10 mM $CaCl_2$ to a protein concentration of 1% (w/w). Rate constants of CiP(wt) and variants were determined by steady-state measurements using hydrogen peroxide (Merck) as the oxidizing substrate and ABTS as the reducing substrate. The reactions were monitored with a Beckmann DU70 spectrophotometer. The concentration of aqueous stock solutions of ABTS was determined spectroscopically at 340 nm using a molar absorptivity of 36 $mM^{-1}cm^{-1}$. The concentration of aqueous stock solutions of hydrogen peroxide was determined spectroscopically at 240 nm using a molar absorptivity of 43.6 $M^{-1}cm^{-1}$. The reactions were performed in potassium phosphate buffer at pH 6.8, and the temperature was 25° C. The ionic strength was kept constant at 0.1 M by regulation of the potassium phosphate concentration. Reactants were used in the following ranges of concentration: Peroxidase ($2\times10^{-9}$–$10^{-10}$M), hydrogen peroxide (10–100 $\mu$M) and ABTS (1 $\mu$M–5 mM). The rate of oxidation of ABTS was monitored at 414 nm with a molar absorptivity of 31.1 $mM^{-1}cm^{-1}$.

ABTS oxidation by peroxidase is described below. Two ABTS molecules are oxidized by an electron transfer to a rather stable radical.

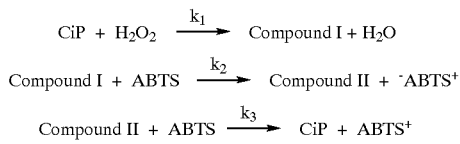

According to Dunford in *Peroxidase in Chemistry and Biology*, J. Evers et al (eds.), Vol. 2, pp. 2–24, CRC Press, 1991, the rate constant for formation of compound I ($k_1$) and for the second oxidation of ABTS ($k_3$) can be determined using the following equation, assuming $k_2>>k_3$;

$$\frac{2[POD]}{v} = \frac{1}{k_3[ABTS]} + \frac{1}{k_1[H_2O_2]}$$

[POD] is the total concentration of peroxidase, v is the initial rate of the oxidation of ABTS. At constant $[H_2O_2]$ plots of 2[POD]/v vs. 1/[ABTS], $1/k_3$ is obtained from the slope and $1/k_1[H_2O_2]$ from the intercept.

TABLE 3

Rate Constants $k_1$ (reduction of $H_2O_2$) and $k_3$ (oxidation of ABTS) for CiP and CiP variants at pH 6.8 and 25° C.

|  | $k_1$ ($\mu M^{-1} s^{-1}$) | % of wt $k_1$ | $k_3$ ($\mu M^{-1} s^{-1}$) | % of wt $k_3$ |
|---|---|---|---|---|
| wild type | 7.9 ± 0.2 | 100 | 35.0 ± 1.0 | 100 |
| G154E | 3.2 ± 0.1 | 41 | 0.6 ± 0.1 | 1.7 |
| G156F | 7.1 ± 0.3 | 90 | 37.0 ± 2.0 | 106 |
| N157E | 5.4 ± 0.1 | 68 | 7.8 ± 0.1 | 22 |
| N157F | 5.8 ± 0.1 | 73 | 26.0 ± 1.0 | 74 |
| G156F-N157F | 5.7 ± 0.2 | 72 | 62.0 ± 2.0 | 177 |
| G154E-G156F-N157E | 3.6 ± 0.3 | 46 | 2.6 ± 0.1 | 7.4 |

The rate constant $k_1$ for formation of compound I at pH 6.8, see Table 3, is 7.9 $\mu M^{-1} s^{-1}$, and $k_1$ is lower for all mutants, especially the mutants containing the G154E substitutions where $k_1$ is less than half of wild type. Wild type and G156F have the same magnitude for the rate constants of ABTS oxidation ($k_3$), see Table 3, Col. 3, and the N157F mutant has a $k_3$ value of 26 $\mu M^{-1}s^{-1}$, which is 74% compared to wt, but the variant G156F-N157F is almost twice as active as wt.

---

What is claimed is:

1. A variant of a parent peroxidase, comprising a substitution of methionine at position 166 with leucine, valine, isoleucine, phenylalanine, or glutamine, wherein the parent peroxidase is encoded by SEQ ID NO:1.

2. A bleaching agent comprising the peroxidase variant of claim 1, optionally in the form of a non-dusting granulate, a liquid, or a protected enzyme.

3. The bleaching agent of claim 2, further comprising one or more substrates for the peroxidase variant.

4. The bleaching agent of claim 3, wherein the substrate is hydrogen peroxide or a hydrogen peroxide precursor.

5. The bleaching agent of claim 4, wherein the substrate is a perborate or percarbonate.

6. The bleaching agent of claim 4, wherein the amount of substrate corresponds to a hydrogen peroxide concentration in the wash liquor of between 10 $\mu$M and 20 mM.

7. The bleaching agent of claim 3, further comprising an oxidisable substrate selected from the group consisting of 7-hydroxycoumarin, vanillin, p-hydroxycinnamic acid, 2,4-dichlorophenol, p-coumaric acid and p-hydroxybenzene sulphonate.

8. The bleaching agent of claim 7, wherein the amount of oxidisable substrate is between about 1 $\mu$M and about 1 mM.

9. A detergent composition comprising the peroxidase variant of claim 1.

10. The detergent composition of claim 9, further comprising one or more substrates for the peroxidase variant.

11. The detergent composition of claim 10, wherein the substrate is hydrogen peroxide or a hydrogen peroxide precursor.

12. The detergent composition of claim 11, wherein the substrate is a perborate or percarbonate.

13. The detergent composition of claim 10, which additionally comprises an oxidisable substrate selected from the group consisting of 7-hydroxycoumarin, vanillin, p-hydroxycinnamic acid, 2,4-dichlorophenol, and p-hydroxybenzene sulphonate.

14. The detergent composition of claim 13, wherein the amount of oxidisable substrate is between about 1 $\mu$M and about 1 mM.

* * * * *